United States Patent
Ignotz et al.

[11] Patent Number: 6,088,606
[45] Date of Patent: Jul. 11, 2000

[54] METHOD AND APPARATUS FOR DETERMINING A DURATION OF A MEDICAL CONDITION

[75] Inventors: Keith Ignotz, Duluth, Ga.; Brian Krantz, Bethesda, Md.; Jonathan Eppstein, Atlanta, Ga.

[73] Assignee: SpectRx, Inc., Norcross, Ga.

[21] Appl. No.: 09/273,493

[22] Filed: Mar. 22, 1999

[51] Int. Cl.⁷ .................................... A61B 5/00
[52] U.S. Cl. ................... 600/316; 600/319; 600/476
[58] Field of Search .................. 600/310, 316, 600/317, 318, 315, 321, 322, 407, 476, 477

[56] References Cited

U.S. PATENT DOCUMENTS

| | | | |
|---|---|---|---|
| 4,852,987 | 8/1989 | Lohmann | 351/221 |
| 4,883,351 | 11/1989 | Weiss | 351/221 |
| 4,895,159 | 1/1990 | Weiss . | |
| 4,930,516 | 6/1990 | Alfano et al. . | |
| 5,203,328 | 4/1993 | Samuels et al. . | |
| 5,369,496 | 11/1994 | Alfano et al. . | |
| 5,427,095 | 6/1995 | Thurston et al. | 600/477 |
| 5,582,168 | 12/1996 | Samuels et al. . | |
| 5,630,423 | 5/1997 | Wang et al. . | |
| 5,735,276 | 4/1998 | Lemelson | 600/476 |

FOREIGN PATENT DOCUMENTS 261957 3/1911 Germany .

*Primary Examiner*—Eric F. Winakur
*Attorney, Agent, or Firm*—Fleshner & Kim, LLP

[57] ABSTRACT

A system and method for determining a duration that a patient has been experiencing a medical condition compares characteristics of fluorescent emissions from a target tissue to expected characteristics. In a system and method embodying the invention, a target tissue is illuminated with excitation light, and fluorescent emissions generated by the target tissue in response to the excitation light are detected. Different characteristics of the fluorescent emissions, including the fluorescent emission intensity or the fluorescent lifetime may be determined. The determined characteristics of the detected fluorescent emissions are then compared to expected characteristics of the fluorescent emissions. The amount that the detected fluorescent characteristics deviate from the expected fluorescent characteristics is used to determine a duration that a patient has been experiencing a medical condition. In some instances, the backscattered portions of the excitation light may also be used to make the determination.

43 Claims, 9 Drawing Sheets

METHOD AND APPARATUS FOR DETERMINING A DURATION OF A MEDICAL CONDITION

BACKGROUND OF THE INVENTION

1. Field of the Invention

The invention is related to an apparatus and methods for determining how long a patient has been experiencing a medical condition. Specific embodiments of the invention can be used to determine the approximate length of time that a patient has been experiencing abnormal blood sugar level fluctuations and thus how closely or often that patient should be tested for diabetes.

2. Background of the Related Art

There are many devices and methods for determining whether a patient has a particular medical condition. However, there are few devices or methods for determining how long the patient has been experiencing the particular medical condition. As a specific example, there are several tests for determining whether a patient has diabetes, but there no devices or methods that are configured to determine how long the patient has been experiencing the diabetic condition.

A diabetic person's body has difficulty regulating blood sugar levels. As a result, a diabetic's blood sugar level fluctuates greatly during each day depending on diet and level of exercise. The effects of these blood sugar level variations are not immediately apparent and tend to build up over time. Early stage complications of diabetes can include vision and circulatory problems. Typically, these early stage complications do not become apparent until a patient's blood sugar level has been out of control for seven to ten years. Thus, it is common for a patient to be approaching the onset of diabetes for many years before diabetes is actually diagnosed.

There are few tests for predicting or determining whether a patient has diabetes (diagnosing diabetes) before actual symptoms begin to appear. One such test is a glucose tolerance test. In this test, a patient ingests a prescribed amount of glucose, and the patient's blood is then periodically sampled and tested to determine the patient's blood sugar level as the patient metabolizes the glucose. However, some patients that show abnormally elevated blood sugar levels during such a test fail to subsequently develop diabetes, thus calling into question the reliability of the test.

A second diagnostic test, called the Islet Cell Antibody (ICA) test, can be used to predict whether a patient will develop Type I diabetes. This test can predict the onset of diabetes by as much as five years before actual symptoms appear. The ICA test, however, is rarely performed because of its complexity, expense and lack of specificity. Furthermore, this test is only useful for predicting Type I diabetes, which only occurs in approximately ten percent of the diabetic patient population.

U.S. Pat. No. 5,203,328 discloses another apparatus and method for determining whether a patient has diabetes. The system and method measure characteristics of the patient's eye that are indicative of diabetes. Specifically, the system and methods illuminate ocular tissue in a patient's eye, and measure backscattered light and fluorescent radiation generated by the ocular tissue in response to the excitation light. The intensity of the backscattered light and fluorescent light at particular wavelengths are then used to determine whether the patient has diabetes. The contents of U.S. Pat. No. 5,203,328 is hereby incorporated by reference.

Similarly, U.S. Pat. Nos. 4,895,159 and 4,883,351 disclose systems and methods for detecting the existence of diabetes using only backscattered light. The contents of these patents are also hereby incorporated by reference.

Although the systems and methods described above can determine whether a patient has been experiencing the symptoms of diabetes, none of the systems or methods are capable of determining how long the patient has been experiencing the diabetic symptoms.

Once it becomes apparent that a patient may possibly develop diabetes, doctors will ask the patient to return for more tests on a periodic basis to determine whether the patient's condition actually develops into the disease. Doctors have certain protocols about how long a patient should wait before being recalled for more testing. If a patient has few symptoms suggestive of diabetes, the patient may not be recalled from more than a year. If several suggestive symptoms are present, the doctor may wish to recall the patient after only a few months. Unfortunately, there is no diagnostic tool for accurately predicting how long a patient may have been experiencing diabetic symptoms, or for determining how great the patient's risk of actually developing the disease. If such a tool were available, it would enable a doctor to tailor his recall and therapy pattern to a patient's needs.

SUMMARY OF THE INVENTION

The invention is a system and method for determining how long a patient has been experiencing a medical condition. In a system and method embodying the present invention, a light source is used to illuminate a target tissue in the patient's body with excitation light. At least one characteristic of light returned from the target tissue is detected, and the at least one characteristic of the returned light is compared to an expected characteristic for returned light. The expected characteristics can be light characteristics one would expect for patients that do not have the medical condition. The results of the comparison are then used to determine whether the patient is experiencing a medical condition, and if so, the duration that the patient has been experiencing the medical condition.

In specific embodiments of the present invention, the returned light can include fluorescent light generated by the target tissue in response to the excitation light. The intensity of the returned fluorescent light can be compared to an expected intensity of fluorescent light for individuals that do not have the medical condition. An amount that the intensity of the actual returned fluorescent light exceeds an expected intensity for returned fluorescent light can then be used to determine a duration that the individual has been experiencing a medical condition.

In embodiments of the invention that detect fluorescent light generated by the target tissue, temporal characteristics of the fluorescent light, instead of intensity, can be detected and used to determine how long the patient has been experiencing a medical condition. The temporal characteristics can be detected by directly measuring the decay time of the fluorescent emissions, by phase shift techniques, by polarization anisotropy techniques, or by any other method of detecting temporal characteristics of the fluorescent light.

In other embodiments of the present invention, the returned light can include backscattered excitation light that returns from the target tissue. Such embodiments may utilize the backscattered light alone to make a determination, or the backscattered light could be used in conjunction with fluorescent light generated by the target tissue to arrive at a determination.

In some embodiments of the present invention, a light source for providing excitation light, and a detector for detecting returned light are arranged as a confocal system. Such a confocal system allows one to interrogate small volumes of target tissue within a larger volume of tissue. Confocal systems allow measurements to be conducted on volumes of tissue that are below the surface of a target tissue.

Also, patient specific information could also be taken into account by a system or method embodying the invention. For instance, a patient's age, sex, and physical characteristics could also be used, in addition to optical information, to determine how long a patient has been experiencing a medical condition. This would allow the system or method to account for age varying characteristics such as fluorescent intensity.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

Preferred embodiments of the present invention will be described in conjunction with the following drawing figures, wherein like reference numerals refer to like elements, and wherein.

DETAILED DESCRIPTION OF PREFERRED EMBODIMENTS

Embodiments of the invention can be used to determine the duration that a patient has been experiencing a medical condition. Preferred embodiments of the invention, like the ones described below, can be used to determine how long a patient has been experiencing diabetic symptoms. Other embodiments of the invention could be used to determine how long a patient has been experiencing other medical conditions.

When a target tissue in a patient's eye is illuminated with certain wavelengths of excitation light, the ocular target tissue will generate fluorescent radiation. Excitation light having wavelengths between approximately 350 nm and 550 nm will cause such fluorescent emissions.

The presence of certain diseases in a patient's body will cause chemical changes in the lens of the eye that will alter how the eye reacts to excitation light. The lenses of cataract patients, for example, become opaque due to lipid peroxidation, protein glycosylation, and the conversion of sulfhydryl bonds to disulfide bonds. Similarly, in patients experiencing diabetes mellitus and galactosemia, the glucose and galactose are converted to sorbitol and dulcitol, respectively. Accumulation of these compounds results in a high osmotic gradient in lenticular cells. Such changes can alter the transmissivity and/or reflectivity of the ocular tissue. Such changes can also alter the intensity of fluorescent emissions generated in response to a given amount of excitation light.

Also, normal age related changes in a patient can cause changes in the opacity and/or reflectivity of ocular tissue, and an intensity of fluorescent light generated in response to a given amount of excitation light. As a patient ages, ocular tissue will tend to become more opaque. Also, an intensity of fluorescent light emitted from ocular tissue in response to a given amount of excitation light will typically increase.

The inventors of the present application have discovered that when a patient's ocular tissue is illuminated with excitation light, characteristics of the returned light can be indicative of the duration that the patient has been experiencing diabetes. In particular, the amount that the characteristics of the returned light deviate from expected characteristics of the returned light for a patient of a similar age that does not have diabetes can be used to determine how long a patient has been experiencing diabetic symptoms. Because a patient's age affects the characteristics of light returned from a patient's eye, the patient's age should be taken into account in making the determination.

Figure 1:
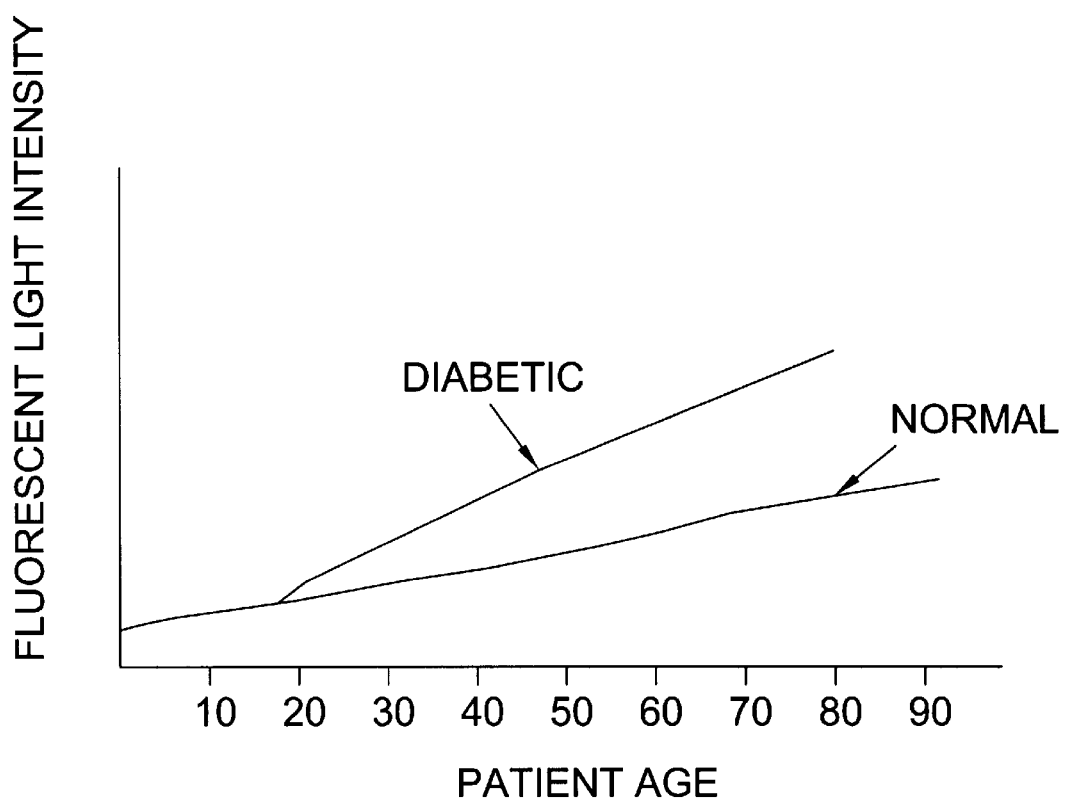
FIG. 1 is a diagram showing the relationship between fluorescent light intensity and patient age for normal patients, and for patients experiencing diabetes.

FIG. 1 shows the relationship between patient age, and an intensity of fluorescent light generated by a patient's ocular tissue when it is illuminated with excitation light. One line in FIG. 1 indicates how the intensity of fluorescent emissions will increase for a normal, non-diabetic patient as the patient ages. A second line indicates how the intensity of fluorescent emissions will increase for a diabetic patient as the diabetic patient ages.

In one preferred embodiment of the present invention, an intensity of fluorescent radiation generated by ocular tissue is used to determine how long a patient has been experiencing diabetes. In such a system and method, an excitation light illuminates a volume of target tissue within a patient's eye. The ocular tissue generates fluorescent radiation in response to the excitation light. A detector then detects an intensity of the fluorescent radiation. If the detected intensity is greater than an expected intensity for a non-diabetic patient of a similar age, one can determine that the patient is experiencing diabetes. The inventor has discovered that the amount that the intensity of the fluorescent radiation exceeds an expected intensity can be used to determine how long the patient has been experiencing diabetes.

The determination of the duration that the patient has been experiencing diabetes is possible because the longer the patient experiences diabetes, the more the intensity of the fluorescent radiation will exceed the expected fluorescent intensity for a non-diabetic patient of a similar age. For example, if the actual fluorescent intensity exceeds the expected intensity by 10%, that patient has probably not been experiencing diabetes for very long. However, if the actual fluorescent intensity exceeds the expected fluorescent intensity by 40%, the patient has probably been experiencing diabetes for several years.

The chart in FIG. 1 shows the normal increase in fluorescent light intensity as a non-diabetic patient ages. The chart also shows that if the patient develops diabetes, the intensity of fluorescent light increases at a greater rate than for a non-diabetic patient. Thus, the longer a diabetic patient experiences the diabetic condition, the more the fluorescent light intensity will exceed the expected fluorescent light intensity for a non-diabetic patient of a similar age.

In the chart shown in FIG. 1, the line corresponding to fluorescent light intensity for a diabetic person indicates that the patient began to experience the diabetic condition at approximately the age of eighteen. If the fluorescent light intensity for this patient was examined when the patient was nineteen, the amount that the fluorescent light intensity exceeds an expected normal fluorescent light intensity would only be a small fraction of the total fluorescent light intensity. However, as the person ages, the percentage by which the fluorescent light intensity exceeds an expected normal fluorescent light intensity continues to grow. Thus, by detecting the fluorescent light intensity, and determining how much the fluorescent light intensity exceeds an expected fluorescent light intensity for a non-diabetic patient of a similar age, one can determine approximately how long the patient has been experiencing the diabetic condition.

Diabetes can cause a whole range of medical complications including circulatory problems and blindness. The effects of diabetes tends to accumulate over time. More and more damage is done to a diabetic's body the longer the patient has the condition. Also, it is quite common for a patient to have diabetes for 7–10 years before the first symptoms of the disease become apparent. At that point, it is difficult, if not impossible to reverse the damage that has already been done. However, if a patient is diagnosed early, before significant damage has occurred, the effects of the diabetic condition can be minimized by controlling the patient's diet and by administering certain drugs.

A system or method embodying the invention, that is configured to predict how long a patient has been experiencing diabetes, is not intended to replace medical diagnostic tests such as the glucose tolerance test. Instead, systems and methods embodying the invention are to be used as a screening tool to determine whether a patient is likely to be experiencing diabetes, and if so, for approximately how long. This information can then be used by a doctor to tailor his recall and testing protocol.

Information as to how long a patient has been experiencing diabetes can be quite useful to medical personnel in prescribing an appropriate course of treatment. If a person has just begun to experience diabetic conditions, relatively simple remedial action, such as a controlled diet, can be used to reduce or eliminate the effects of the diabetic condition. However, if a diagnosis reveals that the person has been experiencing the diabetic condition for a period of seven to eight years, a more aggressive treatment approach should be pursued to prevent the patient from experiencing the more dangerous complications that can result from the diabetic condition.

Although the above description pertains to determining how long a patient has been experiencing diabetes, a system and method embodying the invention could be used to determine how long a patient has been experiencing other medical conditions. Such other embodiments could interrogate target tissues other than a target tissue in a patient's eye. Also, although the above described embodiment compared an intensity of fluorescent light generated by the target tissue to an expected intensity of fluorescent light, a device and method embodying the invention need not operate based on fluorescent light. The intensity of scattered or transmitted light could also be used to determine how long the patient has been experiencing a medical condition. Further, where fluorescent light is used, temporal characteristics of the fluorescent light, instead of intensity, could be used in the determination. In yet other embodiments, as described below, both fluorescent and scattered light could be used to arrive at a determination.

Figure 2:
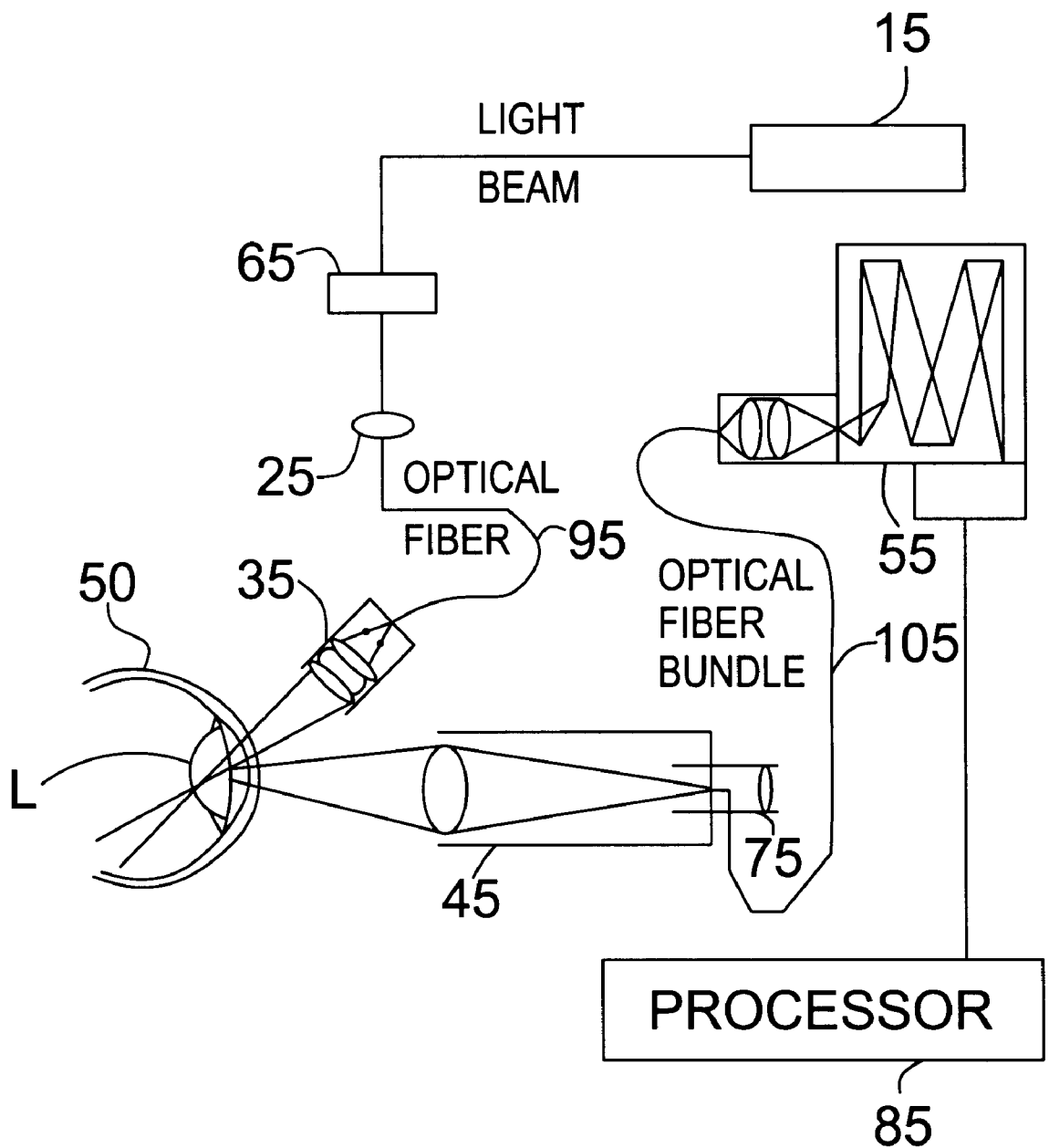
FIG. 2 is a block diagram of a system embodying the present invention.

FIG. 2 shows a diagram of a system embodying the present invention. The system includes a light source 15, and focusing lenses 25, 35 that focus an excitation light beam from the light source 15 onto a target tissue within a patient's eye 50. An optical fiber 95 can be used to convey the light from the light source 15 to and between the focusing lenses 25, 35. Also, an attenuator 65 may be used to reduce a power level of the light generated by the light source 15.

The light source 15 could be a laser, a light emitting diode, or some other type of light emitting device capable of generating light in a relatively narrow wavelength band. The light source could also comprise a broadband light source such as a fluorescent or incandescent light bulb. Such a broadband light source might also be paired with one or more optical filters that are designed to pass only specific wavelength bands of light. The light source 15 could also includes any other type of light source, depending on the wavelengths of interest.

Light returned from the target tissue within the patient's eye 50 is then collected in a collector assembly 45 which directs the light into one or more optical fibers 105 that convey the collected light to a detector assembly 55. The collector assembly 45 may include an eyepiece 75, which permits an operator of the device to view the exact location of the selected target tissue within the patient's eye 50. The light collected by the collector assembly 45 could be a portion of the excitation light that is scattered from the patient's eye 50, or fluorescent light generated by the target tissue in the patient's eye in response to the excitation light.

The focusing lenses 35 for the excitation light and the collector assembly 45 for the returned light are preferably configured in a confocal arrangement so that a relatively small volume of target tissue in the patient's eye 50 is interrogated.

The detector 55 could comprise a spectrometer, a photodetector, or any other type of device capable of sensing the returned light. The detector 55 could be configured to sense the intensity of particular wavelength bands of excitation light that is scattered from the patient's eye 50. The detector could also be configured to detect an intensity of fluorescent light generated by the patient's eye at one or more wavelengths. As explained in more detail below, the detector could also be configured to detect temporal characteristics of fluorescent light generated by the patient's eye 50.

Signals from the detector 55, indicative of characteristics of the returned light, are then passed to a processor 85. The processor 85 utilizes the signals from the detector 55 to determine how long a patient has been experiencing a particular medical condition. As explained generally above, the processor would be configured to compare the detected characteristics of the returned radiation to expected characteristics to determine how long the patient has been experiencing a medical condition. Such a comparison could be made to expected characteristics of the returned light for patients without the condition. Also, to account for age dependent changes, such a comparison could also be made to expected characteristics of the returned light for patients of approximately the same age.

One preferred embodiment of the system shown in FIG. 2 could be configured to determine how long a patient has been experiencing diabetes. In this embodiment, the light source 15 would output excitation light having a wavelength between approximately 430 nm and approximately 480 nm. The excitation light would cause a target tissue within the patient's eye 50 to generate fluorescent light having a wavelength between approximately 500 nm and approximately 600 nm. In a particular preferred embodiment, the excitation light would have a wavelength of approximately 473 nm, which would cause the target tissue in the patient's eye to generate fluorescent light having a peak at approximately 522 nm.

The detector 55 would detect the fluorescent light generated by the target tissue, and provide a signal to the processor 85 which represents the intensity of the fluorescent light. The detected fluorescent intensity information would then be compared to an expected fluorescent intensity for persons of a similar age that do not have diabetes. The difference between the detected fluorescent intensity and the expected fluorescent intensity would be used to determine how long the patient has been experiencing diabetes.

In another preferred embodiment, which may provide a more accurate measurement result, the intensity of the fluorescent light is normalized, using backscattered excitation light, to account for a variety of factors. Such factors could include variations in the opacity of the target tissue, which can vary with a patient's age or physical condition.

In such a system, the detector 55 would be capable of determining an intensity of the fluorescent light generated by the target tissue, as well as an intensity of excitation light that is backscattered from the patient's eye 50. Because the fluorescent light will usually have a different wavelength than the backscattered excitation radiation, the detector 55 can be configured to detect the intensity of light returned from the target tissue at the different respective wavelengths for the excitation light and the fluorescent light. A ratio of the fluorescent light intensity to the intensity of the backscattered excitation light is then determined, thereby normalizing the peak intensity of the fluorescent component. The normalized fluorescent intensity is then compared to an expected normalized fluorescent intensity to determine a duration that the patient has been experiencing a medical condition.

Variations in the opacity or transmissivity of the target tissue can affect the amount of excitation light that is actually delivered to the target tissue, and the amount of fluorescent light that escapes the target tissue and is detected by the detector. Normalizing the fluorescent light with the backscattered light creates a measure of the fluorescent light that automatically accounts for variations in the amount of excitation light energy actually delivered to the target tissue, and variations in the amount of fluorescent light that escapes the patient's eye after the fluorescent light is generated.

In a particularly preferred embodiment of the present invention, where the intensity of fluorescent light returned from the target tissue is normalized, the Rayleigh component of the backscattered excitation light is used for the normalization.

Figure 3:
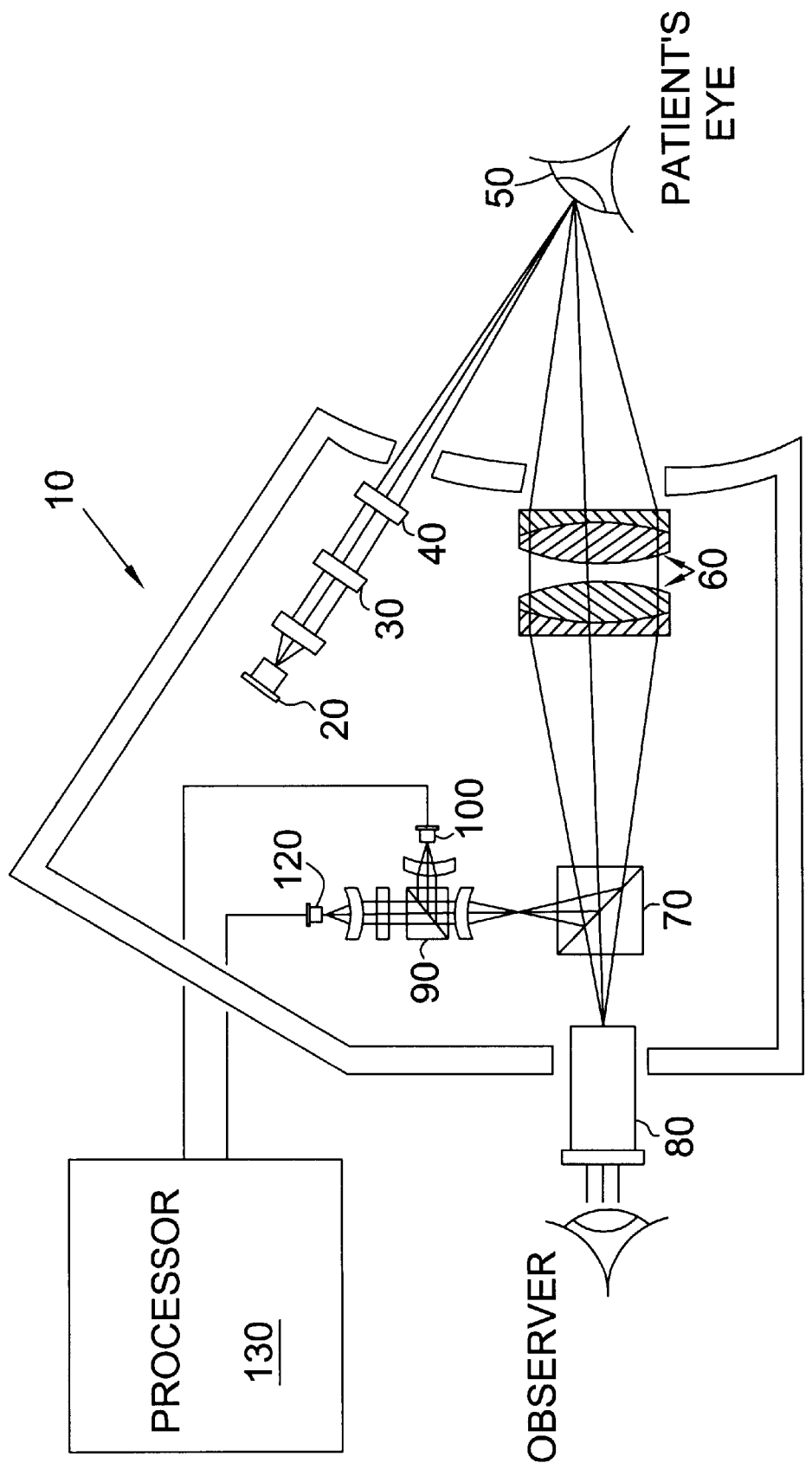
FIG. 3 is a diagram of another system embodying the present invention.

An alternate apparatus embodying the present invention is shown in FIG. 3. In this embodiment, a light source 20 produces excitation light. The light source 20 could be a laser, a light emitting diode, some other type of narrow-band light source, or some type of broadband light source which is coupled to one or more optical bandpass filters. The excitation light is coupled to a frequency altering device 30, to produce excitation light having a desired wavelength. The frequency altering device 30 may be a non-linear frequency doubling device, or any other device capable of changing the frequency of the light produced by the light source 20 so that light having a desired wavelength is generated.

The excitation radiation in the appropriate wavelength band is then directed through an optical delivery system 40 which focuses the excitation light onto a target tissue in the eye 50 of a patient. Return light, which can include a backscattered portion of the excitation light and/or fluorescent light produced in response to the excitation light, is then collected by a lens system 60 which focuses the returned light onto a beam splitter 70.

The beam splitter 70 sends a portion of the returned radiation to an eyepiece 80. An observer can look into the eyepiece 80 to see the target tissue in the patient's eye 50 that is being interrogated. Another portion of the returned radiation is reflected by the beamsplitter 70 towards a second beam splitter 90.

The second beam splitter 90 separates a returned radiation into first and second components having different wavelengths. This allows the system to simultaneously measure the returned light at two different wavelengths. The first component of the returned light will be sent through focusing optics to a first detector 100. The second component of the returned radiation is directed through focusing optics to a second detector 120. Signals from the first and second detectors, indicative of the intensities of the returned light at two different wavelengths, are then sent to a processor 130.

The processor 130 uses the signals from the first and second detectors to calculate characteristics of the returned light. The processor then compares the characteristics of the returned light to expected characteristics, and uses the results of the comparison to determine how long the patient has been experiencing a particular medical condition.

In a particular preferred embodiment of the system shown in FIG. 3, second beamsplitter 90 separates the returned light into two components, one of which is backscattered excitation light, the other being fluorescent light generated by the patient's eye 50 in response to the excitation light. The fluorescent light is focused onto the first light detector 100, which provides a signal indicative of the intensity of the fluorescent light to the processor 130. The backscattered excitation light is focused onto the second detector 120, which provides a signal indicative of the intensity of the backscattered light to the processor 130.

The processor 130 then calculates a ratio of the fluorescent light intensity to the backscattered excitation light intensity. This normalizes the intensity of the fluorescent light. The processor 130 then compares the normalized fluorescent light intensity to an expected normalized fluorescent light intensity to determine a duration that a patient has been experiencing a medical condition, such as diabetes.

In an alternate embodiment of the system shown in FIG. 3, the second beamsplitter 90 could simply split the returned light into two portions. Then, first and second optical bandpass filters could be interposed between the second beamsplitter 90 and the first and second detectors 100, 120. The first and second optical filters would allow first and second wavelength portions of the returned light to pass on to the first and second detectors 100, 120, respectively. Thus, the first and second detectors 100, 120 would provide first and second signals, respectively, indicative of the intensities of the returned light in the first and second wavelength bands.

The light detectors of the systems in FIGS. 2 and 3 can be one or more of several different types of detectors. In any given embodiment, the detector could be a light sensitive diode, with or without a bandpass filter, a spectrometer, or any other type of light detector capable of detecting the intensity of light at particular wavelengths. Examples of two relatively inexpensive light detector assemblies that could be used in a system embodying the invention are shown in FIGS. 4 and 5.

Figure 4:
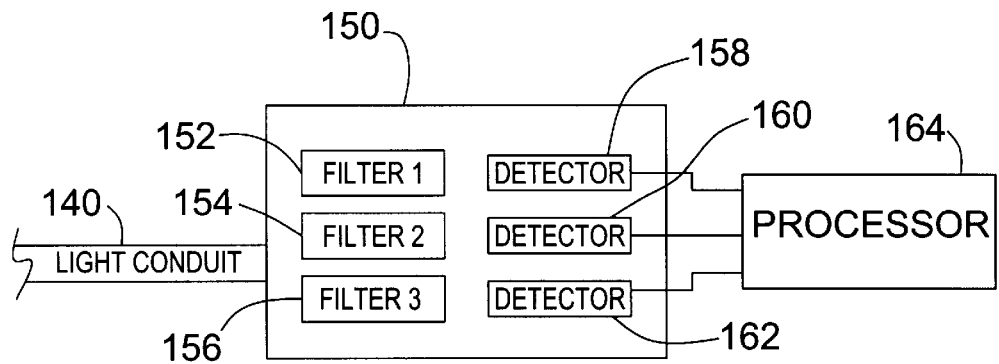
FIG. 4 is a diagram of a detector assembly which can be used in an embodiment of the present invention.
Figure 5:
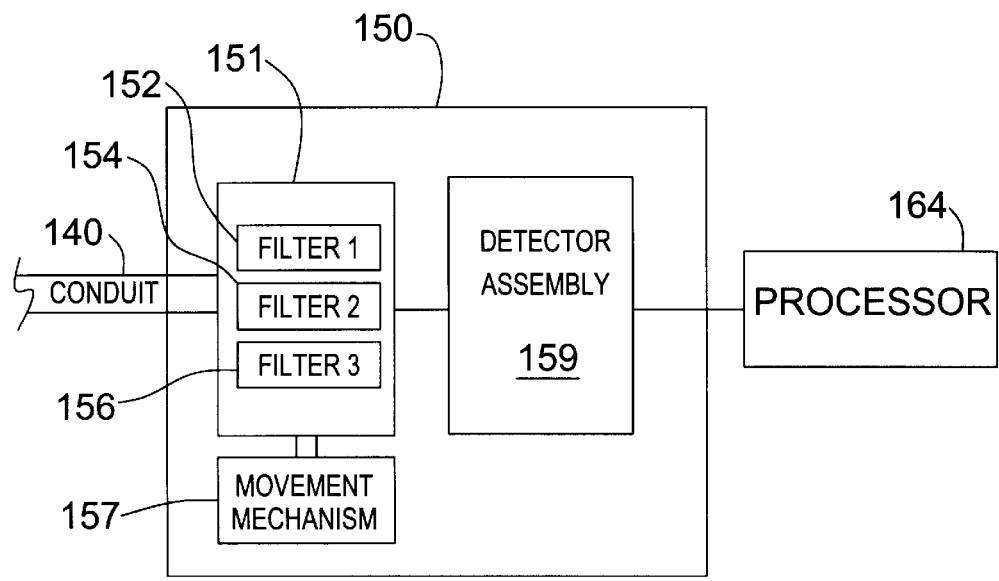
FIG. 5 is a diagram of another detector assembly that can be used in an embodiment of the present invention.

In the detector assembly shown in FIG. 4, light returned from a target tissue is conducted to the detector assembly with a light conduit 140. The detector assembly 150 includes first, second and third filters 152, 154, 156, which correspond to first, second and third detectors 158, 160, 162. Each filter is a bandpass filter designed to pass only a specific, relatively narrow bandwith of light.

The light returned from the target tissue is separated into three portions. A first portion of the returned light is directed to the first filter 152, which passes light in a first wavelength band on to the first detector 158. The first detector 158 provides a first signal indicative of the intensity of the returned light in the first wavelength band, and the first signal is sent to a processor 164. Likewise, the second and third portions of the returned light are directed to the second and third filters 154, 156. The second and third filters pass light in second and third wavelength bands, respectively, to the second and third detectors 160, 162. The second and third detectors 160, 162 provide second and third signals to the processor 164 indicative of the intensity of the returned light in the second and third wavelength bands.

The processor would then calculate the desired characteristics of the returned light using the signals from the first, second and third detectors 158, 160, 162. The processor would then use this information as described above.

A second detector assembly is shown in FIG. 5. In this embodiment, the detector assembly 150 includes a switchable filter assembly 151. The switchable filter assembly 151 includes first, second and third filters 152, 154, 156. Each of the filters 152, 154, 156 can be configured as a bandpass filter which passes only desired wavelengths of returned light.

The filter assembly 151 is connected to a movement mechanism 157. The movement mechanism 157 is designed to selectively position one of the three filters 152, 154, 156 into an optical path passing from the light conduit 140 to the detector assembly 159. By moving the filter mechanism, different ones of the filters can be positioned in the light path. Thus, the detector can receive different wavelength portions of the returned light, sequentially, as the filter assembly 151 is moved.

At any given point in time, the detector 159 will generate a signal indicative of the intensity of the returned light in the wavelength band corresponding to the filter in the light path. As the filter assembly 151 is moved, the detector 159 will sequentially generate different signals indicative of the intensities of the returned light in each of the wavelength bands corresponding to the first, second and third filters 152, 154, 156.

The signals produced by the detector 159 would then be received by a processor 164, and the signals would be used as described above for the systems shown in FIGS. 2 and 3.

The detector assemblies shown in FIGS. 4 and 5 are configured to generate at least two signals indicative of the returned light in at least two different wavelength bands. Although the embodiments shown in FIGS. 4 and 5 have three filters so that intensities can be detected in three different wavelength bands, fewer than three filters, or more than three filters could be provided. For instance, if fluorescent radiation at a particular wavelength is to be normalized with a portion of the backscattered excitation light, only two filters would be necessary. Similarly, if the intensity of backscattered light at more than four wavelengths is to be obtained, more than three filters and three detectors could be provided.

In some of the specific embodiments described above, the intensity of fluorescent light returned from a target tissue is compared to an expected fluorescent light intensity, and any difference between the detected and expected intensities is used to provide an indication of the duration that a patient has been experiencing a medical condition. Although such intensity information can be useful in a large variety of different contexts, there are other ways to measure fluorescent radiation which can provide better and/or different information.

The accuracy of measurements made by fluorescent light intensity based methods are limited by practical issues such as a variation in excitation light intensity and localized changes in fluorophore concentration. In some instances, it may be desirable to measure an intrinsic physical property of the fluorescent radiation, rather than intensity, to eliminate errors that occur due to practical problems. One intrinsic physical property is the fluorescence lifetime, or the decay time of fluorescent light.

Fluorophores in a target tissue emit fluorescent light when excited with excitation light. Usually, the fluorescent emissions will begin at a certain intensity, then slowly decay over time. The duration of the fluorescent emissions of a fluorophore varies depending on the biochemical conditions in the target tissue. Thus, the duration of fluorescent emissions, which is also known as the fluorescence lifetime, can provide valuable information about the condition of the target tissue. In many instances, measuring the temporal characteristics of fluorescent light can provide better, additional or different information that is available through intensity based measurements.

The information provided through the fluorescent lifetime measurements can be used to determine how long a patient has been experiencing a medical condition in much the same way that intensity based measurement information is used. The temporal characteristics of fluorescent radiation generated by a target tissue may be compared to expected temporal characteristics to determine a duration that a patient has been experiencing a medical condition. The use of fluorescent lifetime information may be useful in detecting how long a patient has been experiencing a medical condition in instances where intensity based measurements are not.

The fluorescence lifetime of fluorescent emissions can be detected several different ways. In one method, a very short duration burst of excitation light is directed at a target tissue, and the fluorescent emissions from the target tissue are sensed with a detector. The amplitude of the fluorescent emissions are recorded, over time, as the fluorescent emissions decay. Typically, such fluorescent emissions decay exponentially. The fluorescent emissions may be sensed at specific wavelengths, or over a range of wavelengths. The amplitude decay profile, as a function of time, is then examined to determine the lifetime or decay time of the fluorescent emissions.

Unfortunately, systems configured to directly monitor the amplitude of fluorescent emissions can be quite expensive because of the high cost of light sources capable of generating such short duration bursts of excitation light. Also, detectors capable of accurately measuring the amplitude of fluorescent emissions over the relatively short fluorescent lifetime are also relatively expensive.

In other methods, the temporal characteristics of fluorescent emissions can be indirectly measured through phase shift techniques or polarization anisotropy techniques. These techniques, and systems configured to carry out these measurement techniques are explained below.

As explained above, when a fluorophore is excited with a very short duration pulse of light, the resulting fluorescent emissions decay exponentially. Also, it is known that there is a time lag between the moment that excitation light strikes the fluorophores, and the point in time at which fluorescent emissions begin. If an excitation light is amplitude modulated at a constant frequency, the resulting fluorescent emissions will also appear to be amplitude modulated. The amplitude of the fluorescent emissions will probably be smaller than the amplitude of the excitation light, but the modulated fluorescent emissions will have the same frequency as the modulated excitation light. Because of the time lag between excitation and the beginning of fluorescent emissions, there will be a phase shift between the excitation light and the fluorescent emissions.

Figure 6:
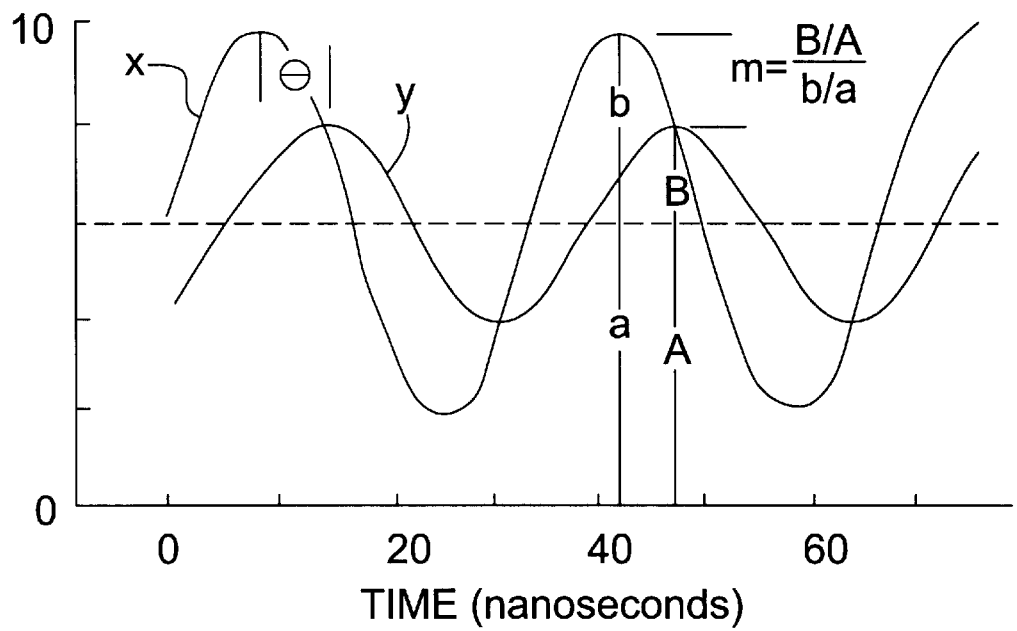
FIG. 6 is a diagram showing the relationship between amplitude modulated excitation light and returned fluorescent light.

FIG. 6 illustrates the concept of illuminating a target tissue with amplitude modulated excitation light, and sensing the resulting fluorescent emissions. In FIG. 6, the waveform X shows the amplitude of modulated excitation light. The amplitude of fluorescent emissions generated in response to the excitation light are shown as the waveform Y. As can be seen in FIG. 6, the peaks of the waveform Y are delayed, or phase shifted, relative to the peaks of waveform X by an amount θ. θ is referred to as the phase shift or angle.

In addition, the amplitude of the fluorescent emissions is smaller than the amplitude of the excitation light. A demodulation factor m represents a ratio of the DC and AC components of the fluorescent emissions relative to the DC and AC components of the excitation electromagnetic radiation.

Figure 7:
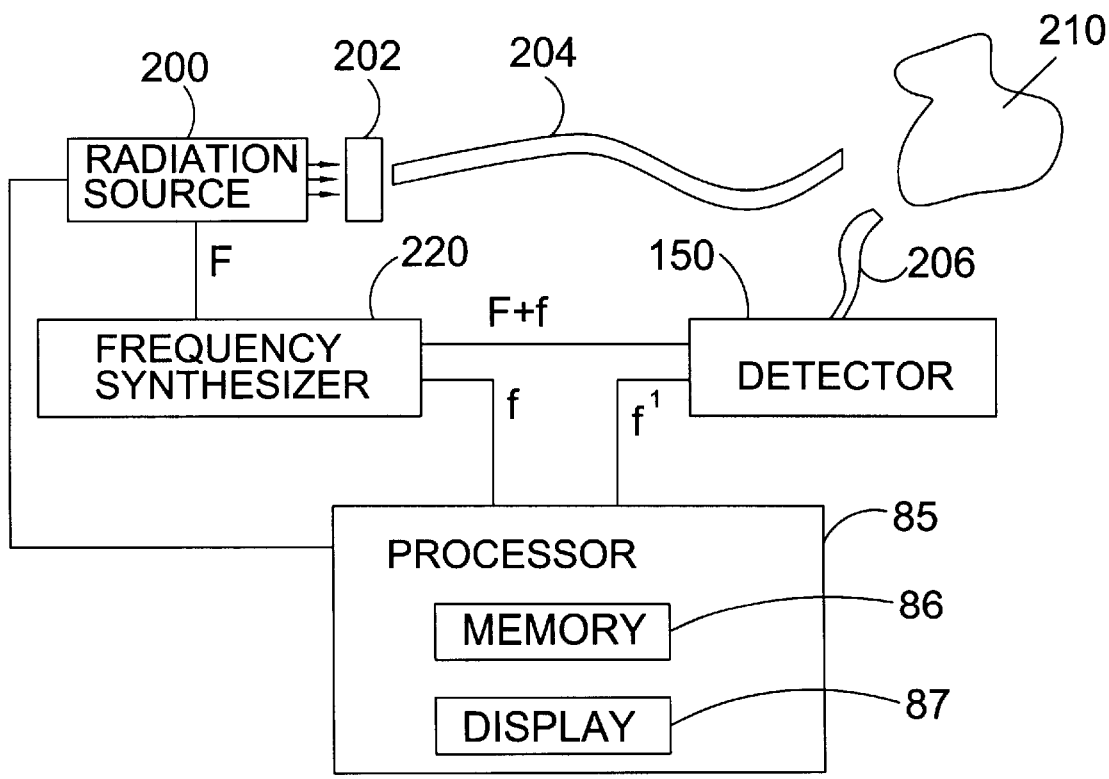
FIG. 7 is a diagram of another system embodying the present invention.

A system embodying the present invention and configured to measuring the temporal characteristics of fluorescent emissions using a phase shift technique is shown in FIG. 7. In this system, a radiation source 200 is connected to a frequency synthesizer 220, and a processor 85. The processor 85 is also connected to a detector 150 configured to detect fluorescent emissions. The detector 150 is also connected to the frequency synthesizer 220. The processor 85 may include a memory 86 and a display 87. In fact, the entire processor may be embodied in a typical personal computer.

The radiation source 200 provides excitation light that is conducted to a target tissue 210. The excitation light may pass through one or more filters or optical focusing devices 202, and may be conducted to the target tissue through one or more optical fibers 204. In alternate embodiments, the excitation light may be emitted from the radiation source 200 in such a manner that the excitation light passes directly from the radiation source 200 to the target tissue 210 without the need for optical fibers 204.

The radiation source 200 could be a laser, a light emitting diode, a fluorescent tube, an incandescent light bulb, or any other type of device that is capable of providing excitation light in the appropriate wavelength range. The radiation source provides amplitude modulated excitation light, which is modulated in response to a signal from the frequency synthesizer 220.

The excitation light delivered to the target tissue 210 causes the target tissue 210 to generate fluorescent emissions. The fluorescent emissions are conducted to a detector 150 through one or more optical fibers 206. In alternate embodiments, the detector 150 may be positioned immediately adjacent the target tissue 210 so that no optical fibers 206 are needed to deliver the fluorescent emissions to the detector 150.

Regardless of whether the fluorescent emissions pass through one or more optical fibers 206, the fluorescent emissions may be focused onto the detector 150 by one or more optical devices such as lenses, mirrors, or beam splitting devices. One or more filters may also be interposed between the target tissue 210 and the detector 150 so that only light in particular wavelengths reaches the detector 150. The detector may be a photomultiplier tube, a photosensitive diode, a charge coupled device, or any other type of electromagnetic radiation sensor.

If the detector is a charge coupled device, it could be located at the distal end of an endoscope or a catheter instrument. In this instance, the charge coupled device would already be located adjacent the target tissue so that the detector could directly sense the fluorescent radiation. The charge coupled device would then need some means for communicating its information to a processor.

The frequency synthesizer 220 is a combination of two high frequency synthesizers that are preferably phase locked. The frequency synthesizer outputs three different signals. A first signal has a frequency F, the second signal has a frequency f, which is lower in frequency than the frequency F, and the third signal has a frequency of F+f, which is slightly higher in frequency than the frequency F. The excitation light from the light source 200 is amplitude modulated at the frequency F. The signal F+f drives the detector 150. The low frequency signal f, is sent as a reference signal to the processor 85.

The embodiment shown in FIG. 7 is a heterodyne system. The detector 150 senses the fluorescent emissions from the target tissue and generates a signal that is modulated at the same frequency as the excitation radiation, or the frequency F. This occurs because, as mentioned above, the fluorescent emissions occur at the same frequency as the modulated excitation light. The detector 150 then uses the higher frequency signal F+f it receives from the frequency synthesizer 220 to convert the signal corresponding to the fluorescent emissions into a low difference frequency signal f', which includes information about the fluorescent emissions. This low frequency signal f' is communicated to the processor 85.

The processor 85 compares the low frequency signal f' to the low frequency signal f, which was generated by the frequency synthesizer 220, to calculate a phase shift θ. The processor 85 may also utilize information about the amplitude of the excitation light that it receives from the radiation source 200, and information about the amplitude of the fluorescent emissions that it receives from the detector 150 to calculate a demodulation factor m. As explained above, the demodulation factor m represents a ratio of the AC component of the fluorescent radiation divided by the DC component of the fluorescent radiation to the AC component of the excitation light divided by the DC component of the excitation light. The demodulation factor can be used in conjunction with the phase difference θ to more accurately determine characteristics of the target tissue.

The processor can utilize the phase difference θ and the demodulation factor m to determine characteristics of the fluorescent emission. The processor 85 can then compare the characteristics of the detected fluorescent emissions to expected characteristics for the fluorescent emissions. Any difference between the detected and expected characteristics can be used to determine a duration that a patient has been experiencing a medical condition.

The above-described system is only one type of heterodyne system that can be used in a system embodying the invention. Other types of heterodyne systems can also be used to determine the phase shift θ and demodulation factor m for the excitation light and fluorescent emissions.

Figure 8:
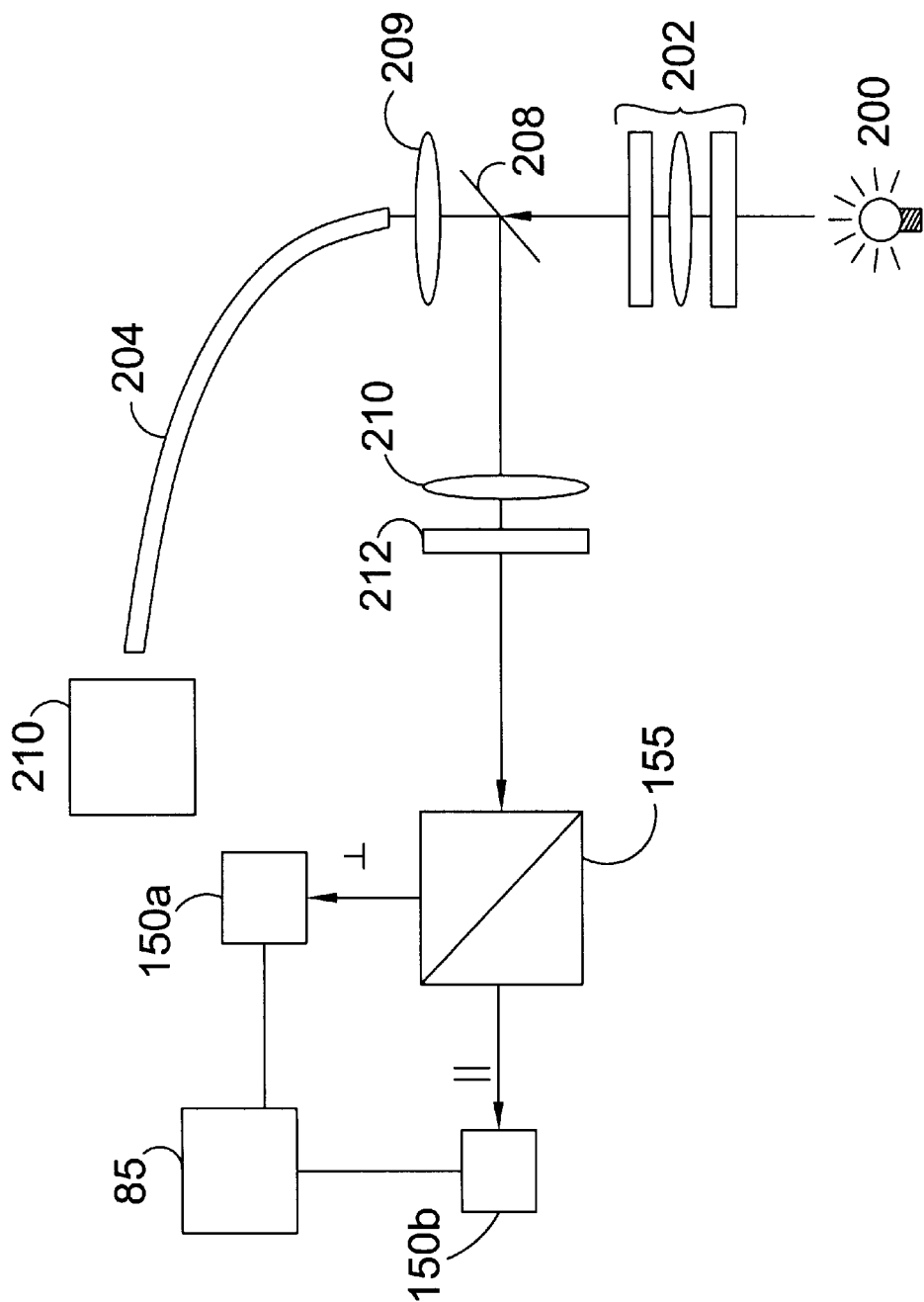
FIG. 8 is a diagram of an additional system embodying the present invention.

An additional alternate system embodying the present invention is shown in FIG. 8. This embodiment measures the lifetime or duration of fluorescent emissions utilizing a polar anisotropy method.

In this system, a polarized beam of excitation light illuminates the target tissue. Only fluorophores that have components of their excitation dipoles arranged parallel to the polarization plane of the excitation light will be excited to emit fluorescent light. Also, the excited fluorophores will emit fluorescent light that is also polarized. As explained above, these fluorescent emissions will have a lifetime dependent on the physio-chemical condition of the target tissue.

Because of Brownian motion, the fluorophores will rotate as they emit fluorescent light. If the excited fluorophores were to emit fluorescent light the instant the excitation light is received, they would begin to generate fluorescent emissions in the same polarization plane as the excitation light. However, as mentioned above, there is a time lag between when the excitation light is received and when fluorescent emissions begin. During this time lag, the Brownian motion causes the fluorophores to rotate out of alignment with the polarization plane of the excitation light. Thus, the initial fluorescent emissions do not occur in the same polarization plane as the excitation light. Also, as the fluorescent emissions from a fluorophore continue, the fluorophore continues to rotate under the Brownian motion. Thus, the polarization plane of the fluorescent emissions continues to rotate until the lifetime of the emissions comes to an end.

The shorter the lifetime of the fluorescent emissions, the greater the amplitude of the fluorescent emissions in polarization planes close to the polarization plane of the excitation light. The longer the lifetime of the fluorescent emissions, the greater the amplitude of fluorescent emissions in a polarization plane perpendicular to the polarization plane of the excitation light. Thus, by detecting the amplitude of the fluorescent emissions in two polarization planes that are parallel and perpendicular to the polarization plane of the excitation light, one can obtain a measure of the fluorescent lifetime of the emissions. This measurement is only possible, however, if the time constant of Brownian rotation is not vastly different from the fluorescent lifetime. For most endogenous fluorophores, this is true. Additionally, exogenous fluorophores can be engineered to satisfy this requirement.

In the system shown in FIG. 8, the light source 200 emits excitation light that passes through one or more optical elements 202 that polarize and/or focus the excitation light. The optical elements 202 may also act as an emission filter so that only certain wavelengths of light are emitted to the target tissue. The excitation light source 200 can be a laser, a light emitting diode, a fluorescent light tube, an incandescent light bulb, or any other type of light emitting device capable of generating appropriate wavelengths of excitation light. Also, in alternate embodiments, the excitation light source 200 could be configured to emit polarized light. In this instance, there would be no need for the optical elements 202 to perform a polarization function.

The polarized excitation light then passes through a dichroic mirror 208, and a focusing lens 209, and then passes to a target tissue 210. Light may be conducted to the target tissue 210 through one or more optical fibers 204.

The fluorophores in the target tissue 210 that are properly aligned with the polarization plane of the excitation light will then be excited to generate fluorescent emissions. The fluorescent emissions will travel back up the optical fiber 204 and through the focusing optics 209. The optical fibers 204 comprise polarization preserving optical fibers so that the polarization of the excitation light and the returned fluorescent emissions is preserved as the radiation is transmitted through the optical fiber 204. In other embodiments, one or more emission optical fibers may be used to transmit the excitation light to the target tissue 210, and a second group of one or more return optical fibers may be used to communicate the fluorescent emissions back to the dichroic mirror 208.

The fluorescent emissions are then reflected by the dichroic mirror 208 through additional focusing optics 210, and optionally through a wavelength filter 212. The fluorescent emissions then enter a beam splitter 155, which separates the fluorescent emissions into two different light beams that are polarized into mutually perpendicular planes. In a preferred embodiment, one polarization plane will be parallel to the polarization plane of the excitation light, and the other polarization plane will be perpendicular to that plane.

The light beam representing fluorescent emissions having a component in a polarization plane parallel to the excitation light is then detected by a first detector 150*b*. Fluorescent emissions having a component in the perpendicular polarization plane are detected by a second detector 150*a*. The first and second detectors 150*a*, 150*b* output signals to a processor 85.

The processor 85 uses the signals from the first and second detectors to calculate an anisotropy factor, which provides a measure of the lifetime of the fluorescent emissions. The processor then compares information regarding the detected fluorescent emissions to expected characteristics, and the results of the comparison are used to determine a duration that a patient has been experiencing a medical condition.

Figure 9:
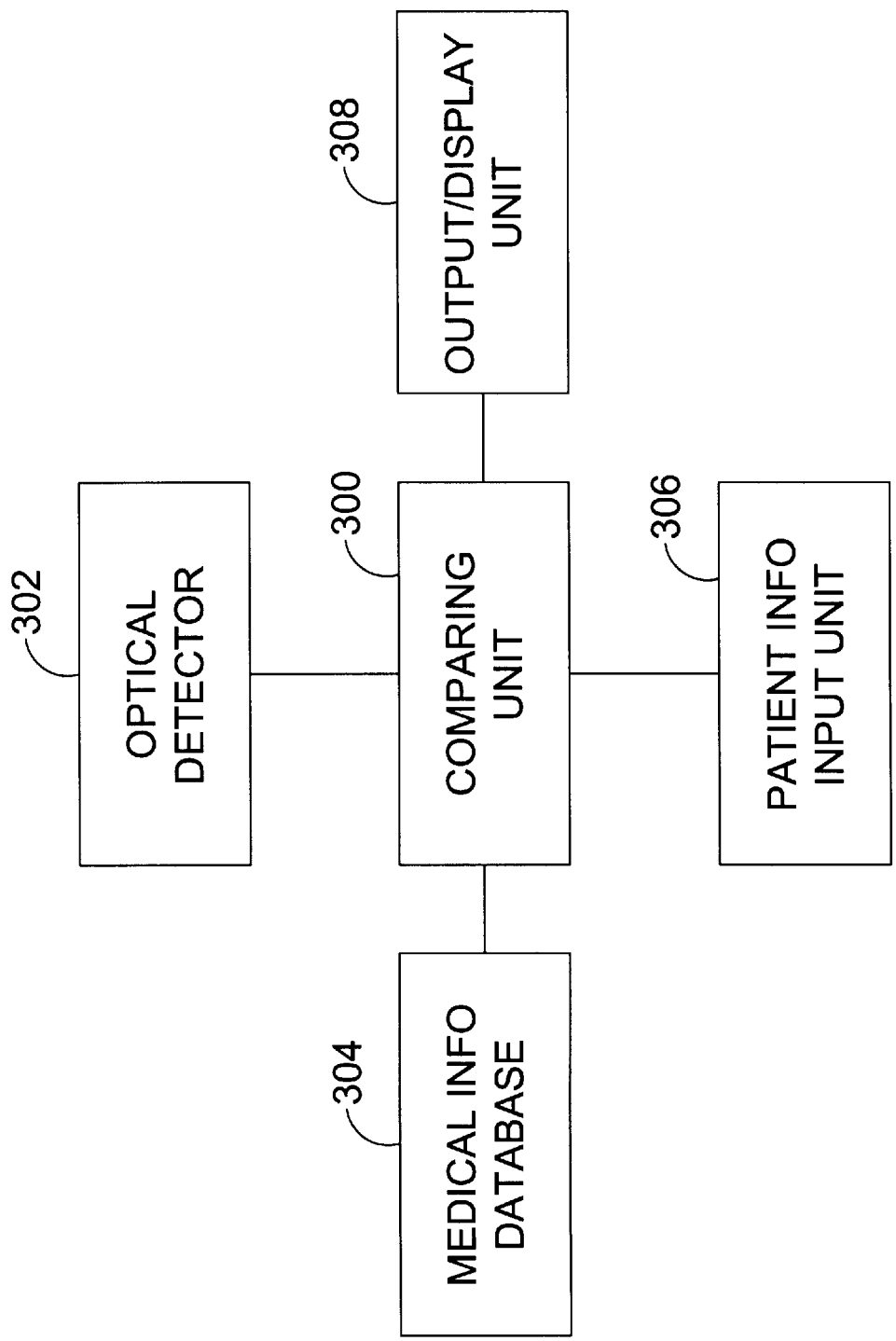
FIG. 9 is a block diagram of another system embodying the invention.

A block diagram of a generalized system embodying the invention is shown in FIG. 9. In this system, a comparing unit 300 is connected to an optical detector 302. The comparing unit 300 could comprise a computer processor and software, or simply an electronic comparator. The optical detector 302 could be any of the detectors described above, or other detector system for determining optical properties of a target tissue.

The comparing unit 300 is also connected to a medical information database 304. The medical information database could be a collection of data stored in an electronic form on a computer readable medium such as magnetic or optical tapes and disks. The medical information database could include information about average expected optical characteristics for healthy people, and similar optical characteristics for people having one or more different medical conditions. The optical information database could also include information about expected ranges of optical characteristics for people that are experiencing one or more medical conditions. This information could be indexed for patient age, sex and/or physical characteristics.

Further, the medical information database could include information about specific patients. This would allow the system to compare detected characteristics of a patient with both known average characteristics for health people, and previous test results from the same patient.

The system also includes a patient information input unit 306 that is also connected to the comparing unit 300. The patient information input unit could comprise a keyboard or a pointing device that would allow medical personnel to input patient-specific information such as patient age, sex or physical characteristics data. The patient information input unit could also include any type of data input devices such as tape or disk readers, that would allow the system to read previously recorded information about a particular patient. This information could be used by the system, in addition to the data from the optical detector 302 and the medical information database 304, to arrive at a determination.

The system also includes an output/display unit 308, connected to the comparing unit 300, for providing the results of a determination. The output/display unit 308 could comprise a printer, a display screen, or a magnetic or optical recording device. Thus, the results of a determination could be printed or displayed on a display screen, or output or recorded in an electronic format.

A system embodying the invention could comprise only the optical detector 302, comparing unit 300 and medical information database 304. The system could be configured so that information from the optical detector 302 is provided to the comparing unit 300, which would then compare the detected information to results previously recorded in the medical information database 304.

In a specific embodiment, the system shown in FIG. 9 could be used for diabetes screening. In this instance, the optical detector 302 could be a confocal system designed to illuminate a patient's ocular tissues with excitation light, and to detect backscattered portions of the excitation light and fluorescent light generated by the ocular tissue in response to the excitation light. Information regarding the intensities of the backscattered and fluorescent light would then be sent to the comparing unit 300.

The comparing unit 300 would then look up expected intensities for the backscattered and fluorescent light in the medical information database 304. The comparing unit 300 would compare the detected intensities to the expected intensities for non-diabetic patients and determine whether the detected intensities exceed the expected intensities by a sufficient margin that the patient is at risk of developing diabetes. If so, the comparing unit would use the amount that the detected intensities exceed the expected intensities to predict how long the patient has been experiencing diabetic conditions. The comparing unit would then output the results of the determinations.

If a patient information input device is also provided, the patient's age and/or other physical characteristics might also be input before the comparing unit attempts to make a determination. This information could be used in the determination process. For instance, if the patient's age is input, the age might be used to look up the expected fluorescent intensity for a non-diabetic patient of a similar age. The age dependent fluorescent intensity would then be compared to the actual detected fluorescent intensity.

Further, as described above, the medical information database 304 could also include information about particular patients. If the medical information database 304 includes optical backscattering and fluorescent information from previous tests on that same patient, this information can also be compared to new test results to determine if there has been significant change since the last test. In diabetes testing, an increase in the intensity of fluorescent emissions that is not due to normal aging would tend to indicate that the patient is continuing to develop diabetic symptoms.

The results of a determination could be output in a variety-of different formats. For instance, the output of a determination might be simply that the patient has an increased risk of developing diabetes. More specific results could include a prediction of how long the patient has been experiencing diabetic conditions. The results of a determination might also include a recommended interval before a second test is performed.

A system as shown in FIG. 9 could also be used to build up a database of optical characteristics that could be used for predicting whether a patient has a medical condition, and if so, how long the condition has persisted. For instance, the medical information database could store the intensities of backscattered and/or fluorescent light generated during a large number of different patient tests, as well as information regarding the patients' ages and physical characteristics. This information could be processed by the comparing unit 300, or by another different processing unit, to calculate average backscattered and fluorescent light intensities for patients of different ages and varying medical conditions. Information built up in this manner could then be used to predict whether a patient has a medical condition, or how long the condition has persisted.

Figure 10:
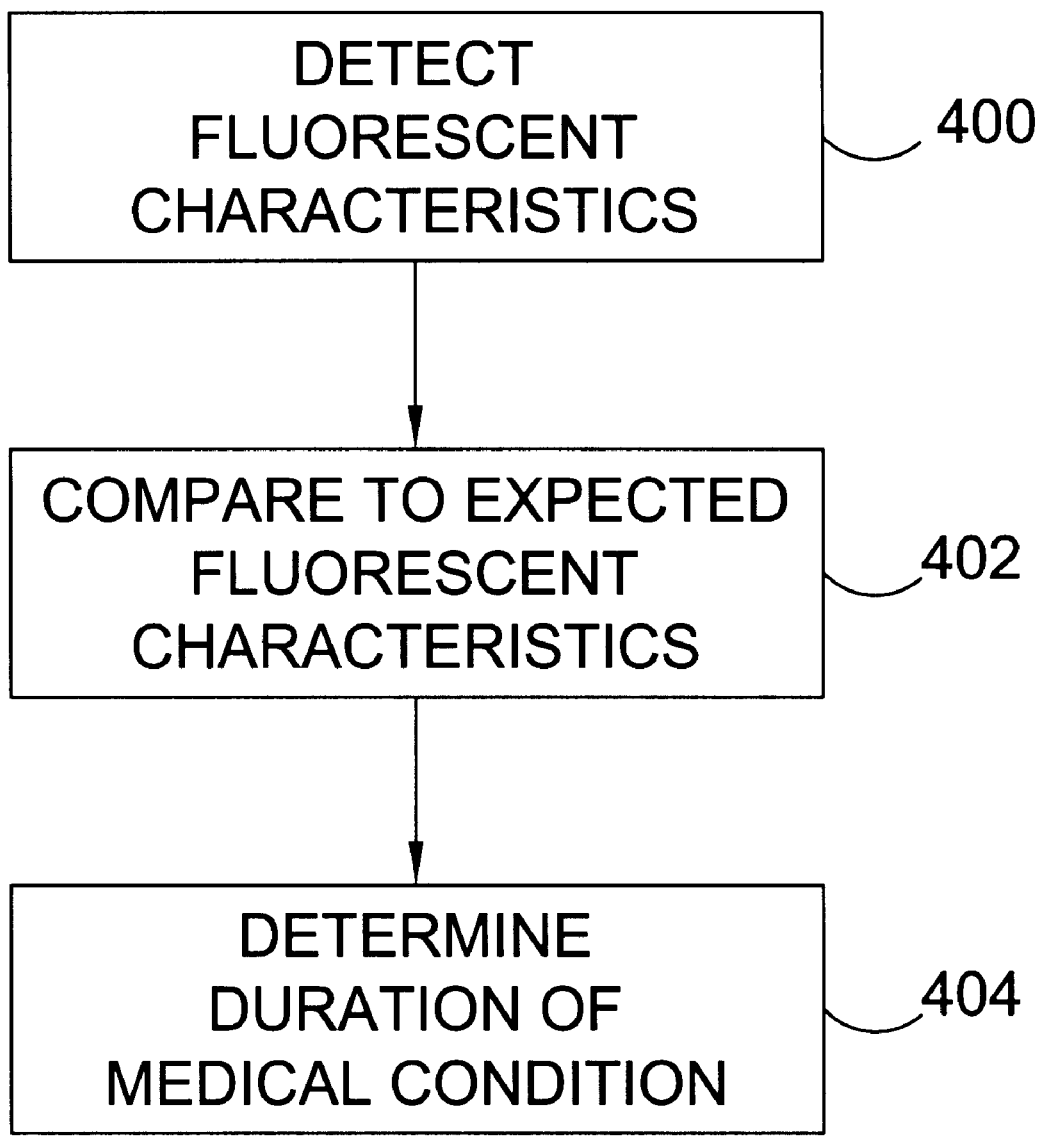
FIG. 10 is a flow chart showing steps of a method embodying the present invention.
Figure 11:
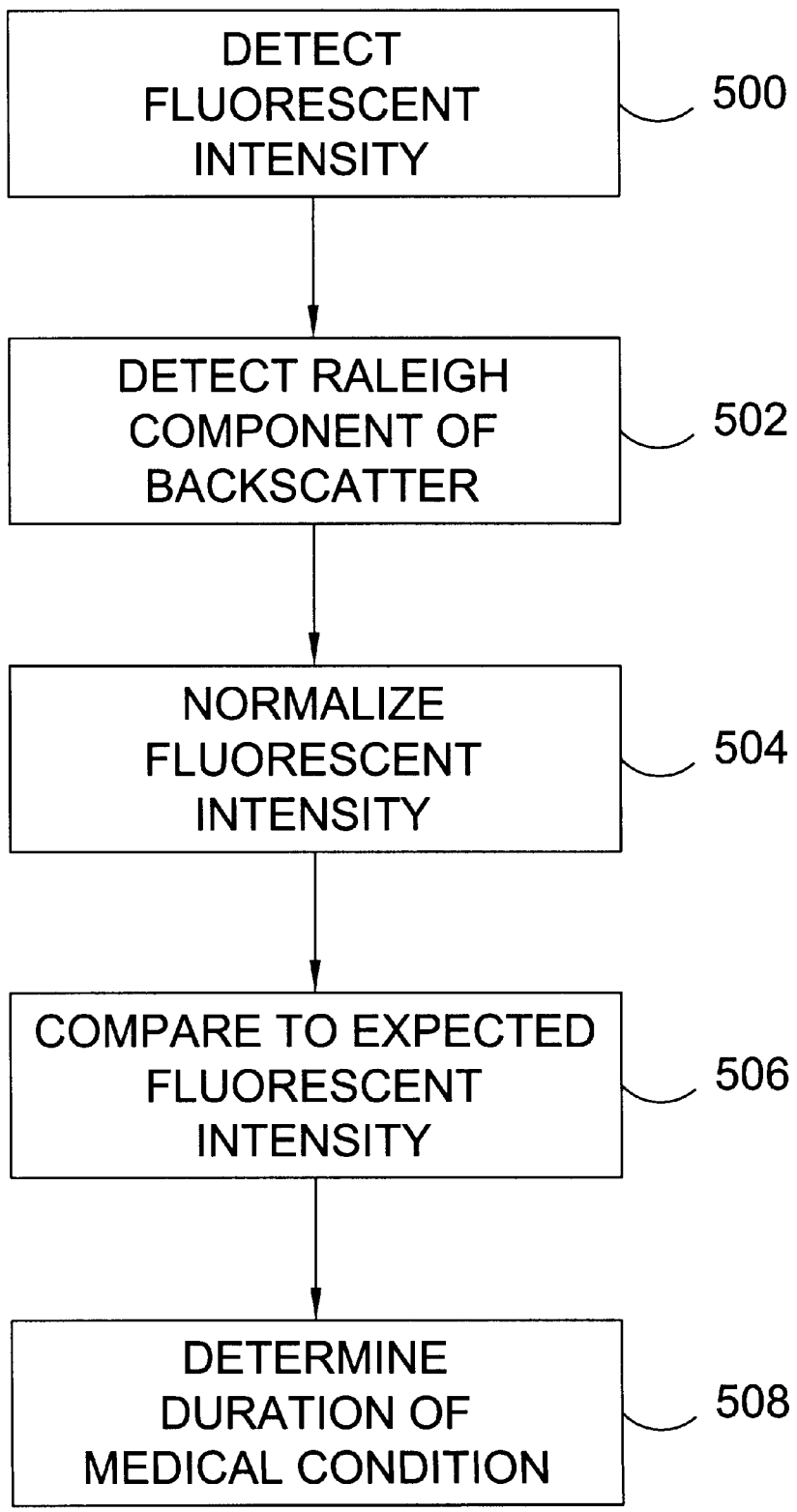
FIG. 11 is a flow chart showing steps of another alternate method embodying the present invention.

Flow charts of methods embodying the present invention are shown in FIGS. 10 and 11.

In the method shown in FIG. 10, characteristics of fluorescent emissions from a target tissue are first detected in step 400. The detected characteristics are then compared to expected characteristics in step 402. In step 404, the duration that a patient has been experiencing a medical condition is determined based on the results of the comparison in step 402.

In the method shown in FIG. 10, the characteristics of the fluorescent emissions that are detected and compared can be the intensity of the fluorescent emissions, the lifetime of the fluorescent emissions, or other characteristics of the fluorescent emissions that are indicative of a duration that a patient has been experiencing a medical condition.

In the method shown in FIG. 11, the intensity of fluorescent emissions is first detected in step 500. In step 502, the intensity of the Rayleigh component of backscattered excitation light is detected. The detected fluorescent intensity is then normalized with the detected Rayleigh component of backscattered light in step 504. In step 506, the calculated normalized fluorescent intensity is compared to an expected normalized fluorescent intensity. The results of this comparison are then used in step 508 to determine a duration that a patient has been experiencing a medical condition.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A method of determining a duration of a medical condition experienced by a patient, comprising the steps of:
   illuminating a target tissue of the patient with excitation radiation;
   detecting fluorescent radiation generated by the target tissue in response to the excitation radiation;
   comparing a characteristic of the detected fluorescent radiation to an expected characteristic of fluorescent radiation; and
   determining a duration of a medical condition experienced by the patient based on results of the comparing step.

2. The method of claim 1, wherein the comparing step comprises comparing a characteristic of the detected fluorescent radiation to an expected characteristic of fluorescent radiation for individuals of approximately the same age as the patient.

3. The method of claim 2, wherein the comparing step comprises comparing a characteristic of the detected fluorescent radiation to an expected characteristic of fluorescent radiation for individuals that do not have the medical condition.

4. The method of claim 1, wherein the detecting step comprises detecting an intensity of fluorescent radiation generated by the target tissue.

5. The method of claim 4, further comprising the steps of:
   detecting an intensity of radiation that is backscattered from the target tissue; and
   normalizing the detected intensity of the fluorescent radiation with the intensity of the backscattered radiation.

6. The method of claim 5, wherein the comparing step comprises comparing the normalized detected intensity of the fluorescent radiation to an expected normalized intensity of fluorescent radiation for individuals that do not have the medical condition.

7. The method of claim 1, wherein the detecting step comprises detecting a characteristic of the fluorescent radiation generated by the target tissue using at least one of an intensity based technique, a phase-shift technique, and a polar anisotropy technique.

8. An apparatus for determining a duration that a patient has been experiencing a medical condition, comprising:
   a source of electromagnetic radiation configured to illuminate a target tissue of the patient with excitation radiation;
   a detector configured to detect at least one characteristic of radiation returned from the target tissue in response to the excitation radiation; and
   a processor configured to compare the at least one detected characteristic of the returned radiation to an expected characteristic of returned radiation and to determine a duration that the patient has been experiencing a medical condition based on results of the comparison.

9. The apparatus of claim 8, wherein the detector is configured to detect an intensity of radiation returned from the target tissue, and wherein the processor is configured to determine a duration that the patient has been experiencing a medical condition based on an amount that the intensity of the detected radiation exceeds an expected intensity of returned radiation.

10. The apparatus of claim 8, wherein the detector is configured to detect fluorescent radiation generated by the target tissue in response to the excitation radiation, and radiation that is backscattered from the target tissue.

11. The apparatus of claim 10, wherein the processor is configured to normalize an intensity of the detected fluorescent radiation based on an intensity of the detected backscattered radiation, and wherein the processor is configured to compare the normalized intensity of the fluorescent radiation to an expected intensity of normalized fluorescent radiation.

12. The apparatus of claim 11, wherein the processor is configured to determine a duration that the patient has been experiencing a medical condition based on an amount that the normalized intensity of the fluorescent radiation exceeds an expected intensity of the normalized fluorescent radiation for individuals that do not have the medical condition.

13. The apparatus of claim 12, wherein the processor is configured to account for an age related increase in the expected intensity of the normalized fluorescent radiation.

14. A system for determining a duration of a medical condition experienced by a patient, comprising:
   means for illuminating a target tissue of the patient with excitation radiation;
   means for detecting fluorescent radiation generated by the target tissue in response to the excitation radiation;
   means for comparing a characteristic of the detected fluorescent radiation to an expected characteristic of fluorescent radiation; and
   means for determining a duration of a medical condition experienced by the patient based on results of the comparing step.

15. An apparatus for determining a duration that a patient has been experiencing abnormal glucose fluctuations, comprising:
   a source of electromagnetic radiation configured to illuminate a target tissue of a patient with excitation radiation;
   a detector configured to detect at least fluorescent radiation returned from the target tissue in response to the excitation radiation; and
   a processor configured to compare a characteristic of the detected fluorescent radiation to an expected characteristic of fluorescent radiation and to determine a duration that the patient has been experiencing abnormal glucose fluctuations based on results of the comparison.

16. The apparatus of claim 15, wherein the processor is configured to determine a duration that the patient has been experiencing diabetes based on an amount that an intensity of the detected fluorescent radiation exceeds an expected intensity of fluorescent radiation.

17. The apparatus of claim 15, wherein the processor is configured to determine a duration that the patient has been experiencing diabetes based on a comparison of temporal characteristics of the detected fluorescent radiation to expected temporal characteristics of the fluorescent radiation.

18. The apparatus of claim 15, wherein the source of electromagnetic radiation is configured to illuminate the target tissue with radiation having a wavelength between approximately 430 nm and approximately 480 nm.

19. The apparatus of claim 15, wherein the detector is configured to detect fluorescent radiation, having a wavelength between approximately 500 nm and approximately 600 nm, that is generated by the target tissue in response to the excitation radiation.

20. The apparatus of claim 15, wherein the detector is configured to detect fluorescent radiation having a wavelength of approximately 522 nm that is generated by the target tissue in response to the excitation radiation.

21. The apparatus of claim 15, wherein the detector is configured to detect fluorescent radiation generated by the target tissue in response to the excitation radiation, and a Rayleigh component of a portion of the excitation radiation that is backscattered from the target tissue.

22. The apparatus of claim 21, wherein the processor is configured to normalize an intensity of the detected fluorescent radiation based on an intensity of the detected Rayleigh component of the backscattered radiation, and wherein the processor is configured to compare the normalized intensity of the fluorescent radiation to an expected intensity of normalized fluorescent radiation.

23. The apparatus of claim 22, wherein the processor is configured to determine a duration that the patient has been experiencing diabetes based on an amount that the normalized intensity of the fluorescent radiation exceeds an expected intensity of the normalized fluorescent radiation for individuals that do not have diabetes.

24. The apparatus of claim 23, wherein the processor is configured to account for an age related increase in the expected intensity of the normalized fluorescent radiation.

25. The apparatus of claim 15, wherein the apparatus is configured to illuminate a patient's ocular tissue.

26. The apparatus of claim 15, wherein the detector is configured to detect fluorescent radiation generated, in part, by glycated proteins, and wherein the processor is configured to determine a duration that patient has been experiencing elevated glucose levels.

27. The apparatus of claim 15, further comprising a storage means for storing fluorescent radiation and backscattered radiation information, and wherein the processor is configured to compare a characteristic of the detected fluorescent radiation to an expected characteristic of fluorescent radiation stored in the storage means.

28. The apparatus of claim 15, further comprising a patient information input device, wherein the processor is configured to utilize patient information input through the patient information input device to determine a duration that the patient has been experiencing diabetes.

29. The apparatus of claim 28, wherein the patient information input device is configured input a patient's age, and wherein the processor is configured to compare a characteristic of the detected fluorescent radiation to an expected characteristic of fluorescent radiation for patient's of a similar age.

30. A method of determining a duration that a patient has been experiencing diabetes, comprising the steps of:
illuminating a target tissue of the patient with excitation radiation;
detecting fluorescent radiation generated by the target tissue in response to the excitation radiation;
comparing a characteristic of the detected fluorescent radiation to an expected characteristic of fluorescent radiation; and
determining a duration that the patient has been experiencing diabetes based on results of the comparing step.

31. The method of claim 30, wherein the comparing step comprises comparing a characteristic of the detected fluorescent radiation to an expected characteristic of fluorescent radiation for individuals of approximately the same age as the patient.

32. The method of claim 31, wherein the comparing step comprises comparing a characteristic of the detected fluorescent radiation to an expected characteristic of fluorescent radiation for individuals that do not have diabetes.

33. The method of claim 30, wherein the detecting step comprises detecting an intensity of fluorescent radiation generated by the target tissue.

34. The method of claim 33, further comprising the steps of:
detecting an intensity of a Rayleigh component of a portion of the excitation radiation that is backscattered from the target tissue; and
normalizing the detected intensity of the fluorescent radiation with the Rayleigh component of the backscattered radiation.

35. The method of claim 34, wherein the comparing step comprises comparing the normalized detected intensity of the fluorescent radiation to an expected normalized intensity of fluorescent radiation for individuals that do not have diabetes.

36. The method of claim 30, wherein the determining step comprises determining a duration that the patient has been experiencing diabetes based on an amount that a characteristic of the detected fluorescent radiation exceeds an expected characteristic of fluorescent radiation for individuals that do not have diabetes.

37. The method of claim 30, wherein the illuminating step comprises illuminating the target tissue with excitation radiation having a wavelength between approximately 430 nm and approximately 480 nm.

38. The method of claim 30, wherein the detecting step comprises detecting fluorescent radiation generated by the target tissue at wavelengths between approximately 500 nm and approximately 600 nm.

39. The method of claim 30, wherein the detecting step comprises detecting fluorescent radiation generated by the target tissue at a wavelength of approximately 522 nm.

40. The method of claim 30, wherein the detecting step comprises detecting fluorescent radiation generated by the patient's ocular tissues.

41. The method of claim 30, wherein the detecting step comprises detecting fluorescent radiation generated, at least in part, by glycated proteins.

42. The method of claim 30, wherein the determining step comprises determining a duration that the patient has been experiencing elevated glucose levels.

43. The method of claim 30, wherein the comparing step comprises accounting for normal age-related increases in fluorescent radiation generated by the target tissue.

* * * * *